US008911343B2

(12) United States Patent
Wiest

(10) Patent No.: US 8,911,343 B2
(45) Date of Patent: Dec. 16, 2014

(54) SYSTEM AND METHOD UTILIZING A SMART PHONE FOR ALLEVIATING PHANTOM LIMB DISCOMFORT

(71) Applicant: Pieter C Wiest, Detroit, MI (US)

(72) Inventor: Pieter C Wiest, Detroit, MI (US)

(*) Notice: Subject to any disclaimer, the term of this patent is extended or adjusted under 35 U.S.C. 154(b) by 144 days.

(21) Appl. No.: 13/656,669

(22) Filed: Oct. 20, 2012

(65) Prior Publication Data

US 2014/0114119 A1     Apr. 24, 2014

(51) Int. Cl.
*A61M 21/02* (2006.01)
*G09B 9/00* (2006.01)

(52) U.S. Cl.
CPC . *A61M 21/02* (2013.01); *G09B 9/00* (2013.01)
USPC ............................................. 600/27; 434/236

(58) Field of Classification Search
USPC ............................................. 600/27; 434/236
See application file for complete search history.

(56) References Cited

U.S. PATENT DOCUMENTS

| 6,425,764 | B1 * | 7/2002 | Lamson ........................ 434/236 |
| 7,771,343 | B2 | 8/2010 | Shiri et al. | |
| 2010/0097438 | A1 * | 4/2010 | Ujii ............................. 348/14.01 |
| 2012/0206577 | A1 * | 8/2012 | Guckenberger et al. ........ 348/47 |

OTHER PUBLICATIONS

Apple introduces the New iPhone 3G. Apple Press info. Jun. 9, 2008. http://www.apple.com/pr/library/2008/06/09Apple-Introduces-the-New-iPhone-3G.html.*

Gawande, A., The Itch, The New Yorker, Jun. 30, 2008, pp. 1-9.
Colapinto, J., Brain Games, The New Yorker, May 11, 2009.
Chan, B. et al., Mirror Therapy for Phantom Limb Pain, New England Journal of Medicine, Nov. 22, 2007, pp. 2206-2207.
Molton, I., Phantom Limb Pain, The Corsini Encyclopedia of Psychology, Weiner, I.B. and Craighead, W.E., editors, John Wiley & Sons, 2010, p. 1230.
Gerding, H. et al. Phantom pain after eye enucleation, Ophthalmologe. Nov. 2003;100(11):943-9. (English abstract via MedLIne).
Anon., Mirror Therapy for Phantom Limb Pain, The Dana Foundation, Mar. 2011. (accessed online from https://www.dana.org/media/detail.aspx?id=31052, Sep. 16, 2012).

* cited by examiner

*Primary Examiner* — Christine Matthews
*Assistant Examiner* — Joshua D Lannu
(74) *Attorney, Agent, or Firm* — Kartar Arora

(57) ABSTRACT

A system and method for alleviating phantom limb discomfort using a smart phone equipped with a camera and having a digital imaging program or application for acquiring, processing, and displaying digital images. The digital imaging program is first used to acquire a comprehensive, composite moving image of the subject's body. Next, using the program, the moving image of subject's half-torso adjacent the limb of the amputation site, and any remaining amputation-site limb, is deleted and replaced with the moving mirror-image of the complementary portion of the subject's torso and its adjacent healthy limb. The composite image is then melded and subsequently displayed for the subject's viewing. Alleviation of the subject's phantom limb discomfort results from viewing the composite imagery on subject's smart phone. This alleviation occurs by means referred to as Acquire, Flop, Meld and View.

8 Claims, 10 Drawing Sheets

© 2011 Pieter Wiest

FIG. 9

(This flow chart pertains to the embodiment spoken of in this application's "Detailed Description Of An Illustrative Embodiment.")

START

Utilize, on a smart phone's view screen, an outline diagrammatic depiction of the human figure that allows for the correct placement of the patient (subject) in relation to the digital recording device -- the same above-mentioned smart phone. (This diagrammatic depiction is an aspect of the program, which is a part of the present invention. The mentioned program, and all of its attendant functions, is mounted on this same smart phone. The program's processor is that of the smart phone. The entire program may, alternatively, be mounted on any suitable computer.)

Produce the streaming color digital-imagery of the subject, undertaken by means of the digital imaging device -- the smart phone -- as he faces the phone's camera. (This imagery is to be that of the normal, healthy limb, and all other viewable aspects of the subject's head, face, and body, including imagery of any remaining portions of the like opposed limb. This last mentioned limb is that limb that has experienced a hand amputation. All actions required by the subject during the production of this streaming video are articulated in the program.)

Utilize the bisection lines, and other digital-manipulation functions of the invention's program, to achieve removal of the streaming color imagery of the right-hand side half-torso and limb.

Utilize the bisection lines, and other digital-manipulation functions of the invention's program, to achieve flopping of the streaming color imagery of the left-hand side half-torso and limb. (This left-hand side imagery will be maintained in its original position, as well.)

Utilize digital-manipulation functions of the invention's program to achieve melding of the newly arranged streaming color imagery.

Display the final, streaming therapeutic imagery now made available to the subject by means of the smart-phone mounted program of the present invention. (This therapeutic video is free of diagrammatic depictions, bisection lines, prompts, and all other program notes. A streaming color video of the subject, undertaking therapeutic actions, is thus ready to be viewed.)

END

© 2011 Pieter Wiest

SYSTEM AND METHOD UTILIZING A SMART PHONE FOR ALLEVIATING PHANTOM LIMB DISCOMFORT

FIELD OF THE INVENTION

The present invention relates to a system and a method for alleviating phantom limb discomfort. More particularly, the present invention pertains to a system and a method for alleviating phantom limb discomfort by the use of a smart phone or similar device; said phone to be used to acquire images of a subject with phantom limb discomfort, and to digitally process these images, and to display these images as composite images of the subject in order to provide relief from phantom limb discomfort.

BACKGROUND OF THE INVENTION

Phantom limb discomfort refers to a type of discomfort that seems to arise in a limb or other body part, which limb or body part in fact, is not present. One type of phantom limb discomfort, called phantom limb pain (PLP), refers to pain that seems to arise in a limb or other body part, which limb or body part in fact, is not present. These pains often occur when a limb or other body part has been removed by amputation. Phantom limb pain duplicates nearly all of those forms of pain associated with other, more conventional trauma. Another type of phantom limb discomfort, called phantom limb sensation (PLS), also seems to arise in an absent limb or other body part. These sensations result in a subject's experiencing one or more perceptions such as those of a limb or body part that is being twisted, crushed, or experiencing inappropriate distortion. Mild electrical shock, cramping, clenching, itchiness, tingling, numbness, dampness, heat, cold, swelling, shrinking, or inappropriate motions such as swinging, are also noted. Perceptions of PLS are less noxious than those of PLP, not only in their various types, but in their intensity as well.

Clinicians report that PLP or PLS is present as an aftereffect in the majority of all amputations. Doctors caring for returning veterans at Walter Reed Army Medical Center have suggested the percentage of PLP-involvement to be above 90%. PLP and PLS are often described by those suffering from them as ranging from mild to excruciating. Professionals working in the areas of neuroscience, academia, and medicine have little doubt that PLP can be a devastating burden for its sufferers. Finally, PLP and PLS are thought to play a role, not infrequently, in incidents of suicide. Also, PLP and PLS are no small matter in the world health-care picture; worldwide, over 400,000 amputations occur yearly, due to snakebite alone.

Mirror therapy, currently utilized by caregivers and their patients around the world, is widely found to be helpful in dealing with a broad array of diseases and disorders that present with pain. Information regarding mirror therapy is given in the publication "The Brain" from the Dana Foundation, which publication may be viewed at < http://www.dana.org/brain.aspx>. The entire disclosure of "Mirror Therapy for Phantom Limb Pain" from the publication "The Brain" is incorporated herein by reference.

In one use of mirror therapy, a widely used non-invasive treatment for PLP and PLS, a patient with PLP or PLS places the unaffected limb in front of a mirror. The other limb, in this instance an arm with a missing hand in which phantom-hand PLP or PLS is perceived as originating, is kept out of view behind the mirror. The unaffected limb's hand is then moved in a manner the patient would wish to see duplicated in the phantom hand, were that hand still present. It has been found that through proper concealment of the arm with the missing (phantom) hand, and through adjustment of their head and eyes relative to the minor, a majority of patients experience remediation of PLP or PLS in the hidden limb's phantom hand at very nearly the exact instant in which they successfully perceive and believe the image in the mirror to be that of their amputated hand, now restored to healthy activity.

Phantom limb discomfort, PLP or PLS, is real pain and real sensation. It is experienced where all pain and sensation are experienced, that is, in the brain. But unlike conventional pain or conventional sensations, PLP and PLS are real events that seem to emanate from an unreal place. Resolution of this neurological paradox, from which phantom limb discomfort arises, is achieved when the brain believes it sees its phantom limb restored to its former healthy status.

A treatment for some forms of pain involves the use of virtual reality (VR) technologies entailing the use of computers, multimedia peripherals, and digital imaging software to produce a virtual environment that provides proposed relief of pain. Examples of VR technologies for treatment of pain are given in U.S. Pat. No. 7,771,343. The entire disclosure of '343 patent is incorporated herein by reference.

At the present time, there are several disadvantages to the use of VR technology in the treatment of phantom limb discomfort. These include high cost, the need to have professional practitioners present, and the need for specific environments such as a hospital or laboratory. Also, exertive physical and mental demands may be placed on the patient during some VR pain treatments. There is a need to provide systems and methods for treatment of phantom limb discomfort that are easily realized, affordable, and do not need the presence of specialists for the operation and use of such systems and methods. As well, a therapeutic treatment is needed that is handy, nearby, and always available. Also desirable is the obtaining of therapeutic outcomes without continuous and concerted physical and mental exertion by the patient, which exertion is called for in interface-effectuated therapies. The present invention provides alleviation of phantom limb discomfort through novel systems and methods that overcome many disadvantages in the prior art.

BRIEF DESCRIPTION OF THE DRAWINGS

In order to provide understanding of the invention, it will now be described with reference to the following illustrations showing a preferred embodiment of the invention. The embodiments shown here are for the purpose of illustration only and should not be construed to provide details of each and every element of the invention. In this respect the illustrations shown should not be used to limit the scope of this invention as these illustrations provide embodiments to persons of ordinary skill in the arts.

FIG. 9 is a flow chart of the inventive system.

DEFINITIONS

Figure 1:
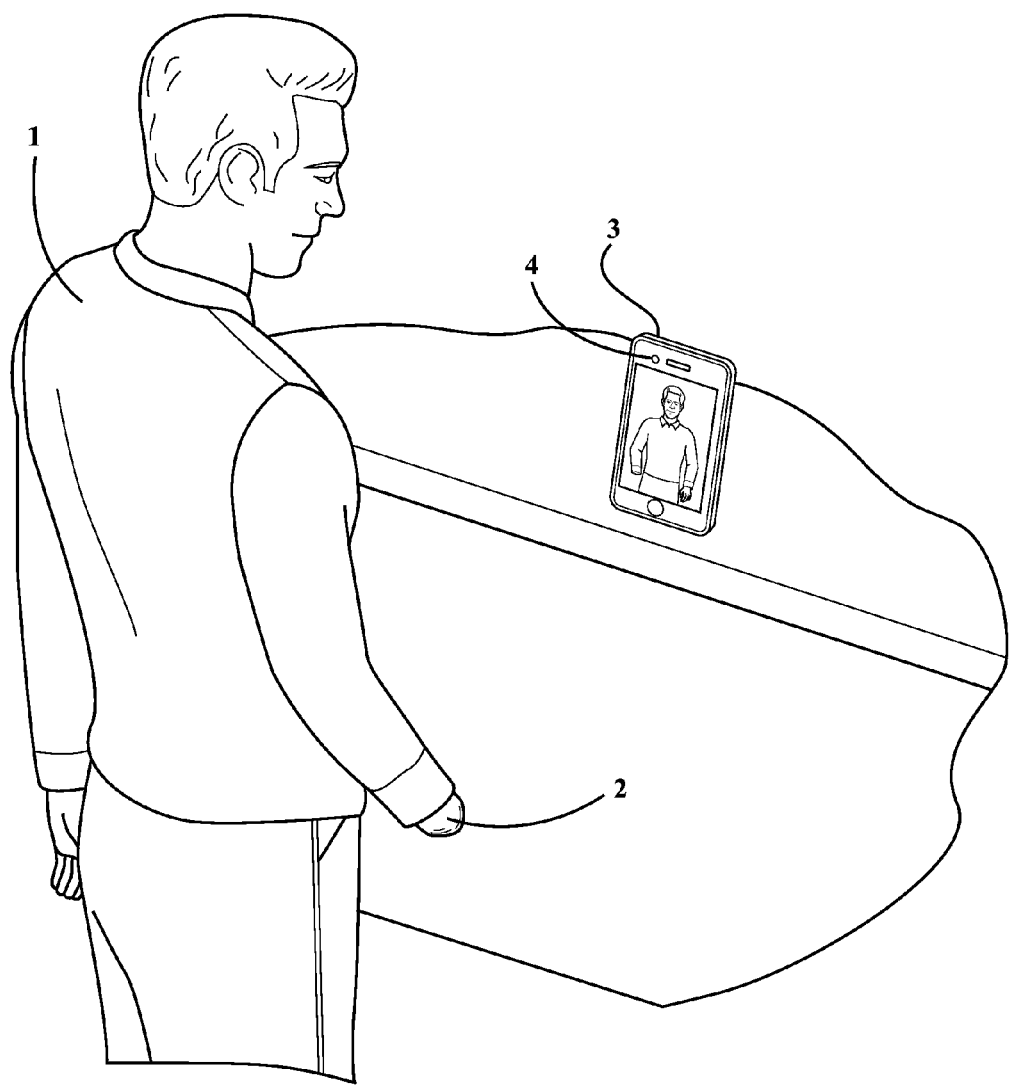
FIG. 1 shows a phantom limb discomfort (PLP or PLS) sufferer 1 with a missing right hand 2 standing and facing a smart phone 3 containing a digital camera 4.
Figure 2:
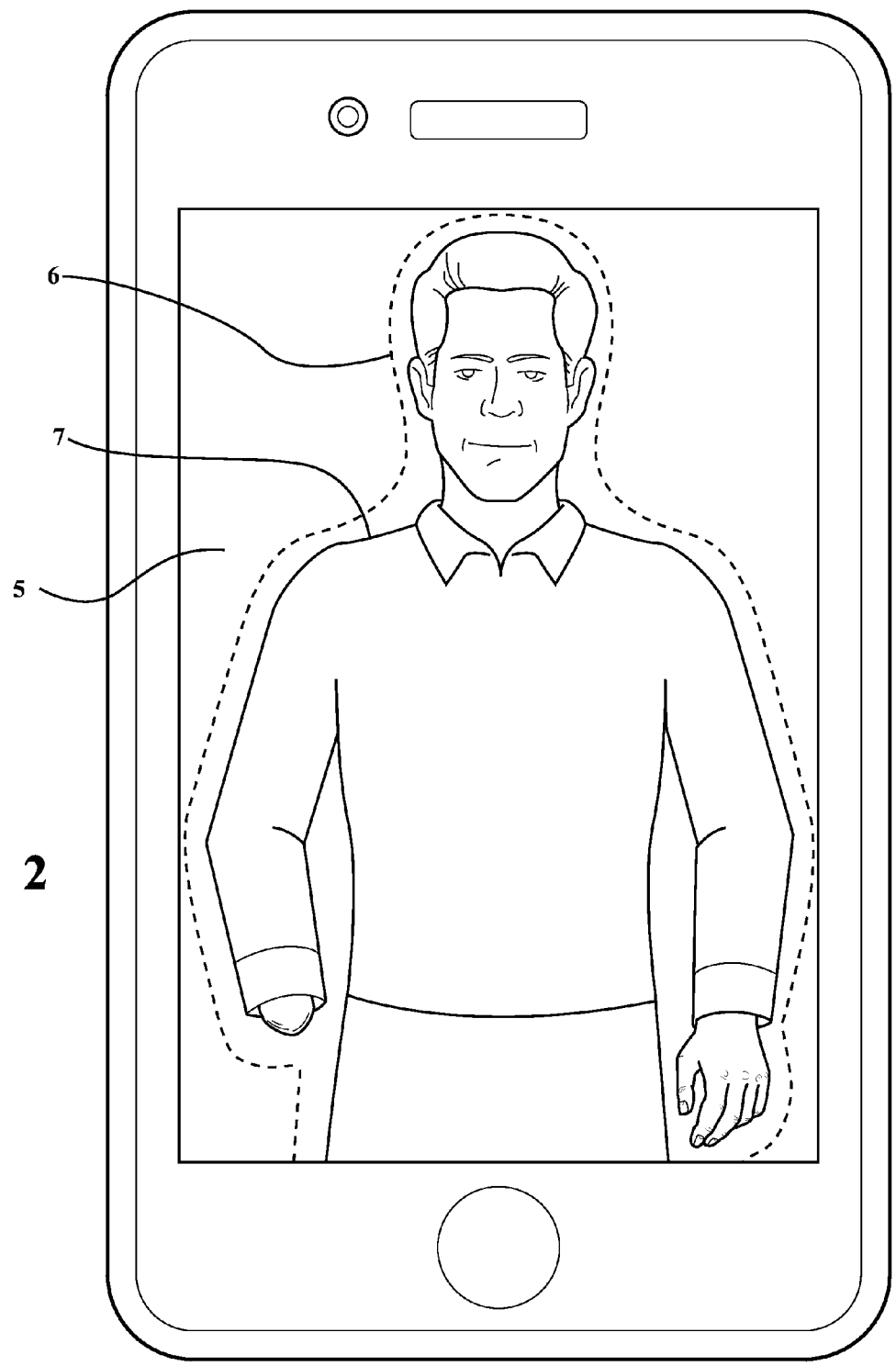
FIG. 2 is a view-screen 5 of the smart phone with an outlined diagrammatic image of the human FIG. 6, and the digital color image 7 of the patient (subject), which image fits within the diagrammatic image.

"Phantom Limb Discomfort" as used in this invention refers to a type of discomfort that arises in limb or other body part, which limb or body part in fact, is not present. One type of phantom limb discomfort, called phantom limb pain (PLP), refers to pain that seems to arise in a limb or other body part, which limb or body part in fact, is not present. Another type of phantom limb discomfort, called phantom limb sensation (PLS), also seems to arise in an absent limb or other body part. These sensations result in a subject's experiencing one or more perception such as those of a limb or other body part that is being twisted, crushed, or experiencing inappropriate distortion. Mild electrical shock, cramping, clenching, itchiness, tingling, numbness, dampness, heat, cold, swelling, shrinking, or inappropriate motions such as swinging, are also noted. Perceptions of PLS are less noxious than those of PLP, not only in their various types, but in their intensity as well.

"Composite Image" as used here refers to an image resulting from the combining of a portion of an image, utilized as originally acquired, with portions of that image that have been altered.

"Flopping" describes the reversing of an image along a vertical axis. A flopped image may be said to be a mirror image of its respective original.

"Melding" refers to the process of retouching all the necessary edges in a streaming composite image, as with those edges resulting from the removal of a half-torso and limb, and the flopping of a half-torso and limb. Melding, which can also be called stitching or patching, results in a very believable and therapeutic video of the subject. After melding, every pixel within the flopped segment of the healthy-side half-torso and arm remains in the identical relative position to every other pixel in this healthy segment, as when said pixels were originally visually acquired.

"Smart Phone" refers to a mobile telephone with sufficiently advanced computing means as to allow for the acquiring, processing, and displaying of visual images. Examples of appropriate smart phones are camera equipped mobile telephones available as iPhone (Apple), Galaxy (Samsung), Droid (Motorola), Optimus (LG), etc.

"Digital Imaging Program" as used here means a set of instructions comprising those necessary for the acquiring, processing, and displaying of digital visual images. For smart phones these programs are called Applications or Apps. Examples of programs suitable for such digital imaging activities include Adobe Photoshop (Adobe), Corel Video Studio (Corel Corporation), etc.

DETAILED DESCRIPTION OF THE INVENTION

A portion of the disclosure of this invention contains material that is subject to copyright protection. The copyright owner has no objection to facsimile reproduction, by anyone, of the patent document or the patent disclosure as it appears in the United States Patent and Trademark Office patent file or records, but otherwise reserves all copyright rights whatsoever.

The invention described herein provides a system and a method for a phantom limb discomfort sufferer to utilize, not a minor, but digital imagery arrayed on a view-screen. By viewing such imagery, the patient can alleviate his phantom limb discomfort (PLP or PLS).

The present invention provides a system and a method for alleviating phantom limb discomfort (PLP or PLS). More particularly, the present invention provides a system and a method for alleviating phantom limb discomfort by using smart phones and similar devices to acquire images of a subject with phantom limb discomfort, and to digitally process said acquired images to obtain composite images, and to display said digitally processed composite images for the subject's viewing. Phantom limb discomfort is thereby alleviated.

One of the objectives of this invention is to provide a system and a method for alleviation of phantom limb discomfort using smart phones for the acquiring, processing, and displaying of digital images of a subject suffering from phantom limb discomfort. The alleviation of phantom limb discomfort is considered to result from subject's viewing of composite images of himself wherein the area of the phantom, the missing body part, is replaced with a mirror image of the complementary healthy body part. The alleviation of phantom limb discomfort is further thought to result from the feedback provided by the self-created image, which image contains the mirror imaged body part as said body part exhibits healthy behavior and stimulates accompanying neurophysiological and psychological processes in the brain.

According to a first aspect of the present invention there is provided a method for alleviating phantom limb discomfort (PLP or PLS) in a subject's phantom limb or other body part comprising:

acquiring a moving image of a continuous portion of the subject that consists of the half-torso adjacent the limb of the amputation site and any remaining amputation-site limb, as well as of the continuous complementary portion of the torso and its adjacent healthy limb, in a particular mode of use;

using a digital imaging program or application to obtain a composite moving image of the subject by deleting the moving image of the half-torso adjacent the limb of the amputation site and any remaining amputation-site limb;

placing a moving flopped image of a continuous complementary portion of the subject's torso and its adjacent healthy limb, in the particular mode of use, in place of the deleted moving image of the half-torso adjacent the limb of the amputation site and any remaining amputation-site limb;

melding the flopped moving image of the complementary portion of the torso and its adjacent healthy limb with the original moving image of the healthy-side torso and limb; and displaying the resultant composite moving image of the subject for subject's viewing.

According to a second aspect, the present invention provides a system for alleviating phantom limb discomfort (PLP or PLS) in a subject's phantom limb or other body part comprising:

a smart phone for acquiring a moving image of a continuous portion of the subject that consists of the half-torso adjacent the limb of the amputation site and any remaining amputation-site limb, as well as acquiring a moving image of a continuous complementary portion of the torso and its adjacent healthy limb, in a particular mode of use;

a digital imaging program or application to obtain a composite moving image of the subject by deleting the moving image of the half-torso adjacent the limb of the amputation site and any remaining amputation-site limb, and by placing a flopped moving image of a continuous complementary portion of the torso and its adjacent healthy limb, in the particular mode of use, in place of the deleted moving image of the half-torso adjacent the limb of the amputation site and any remaining amputation-site limb;

melding the flopped moving image of the complementary portion of the torso and its adjacent healthy limb with the original moving image of the healthy-side torso and limb; and a smart phone for displaying the resultant composite moving image of the subject for subject's viewing.

According to yet another aspect of this invention there is provided a method for alleviating phantom limb discomfort (PLP or PLS) in a subject's phantom limb or other body part comprising:

acquiring a moving image of a continuous portion of the subject that consists of the subject's half-torso adjacent the limb of the amputation site and any remaining amputation-site limb, as well as of the continuous complementary torso and its adjacent healthy limb, in a particular mode of use;

using a digital imaging program or application to obtain a composite moving image of the subject's body by deleting a moving image of the subject's half-torso adjacent the limb of the amputation site and any remaining amputation-site limb;

placing a flopped moving image of a continuous complementary portion of the torso and its adjacent healthy limb, in the particular mode of use, in place of the deleted moving image of the half-torso adjacent the limb of the amputation site and any remaining amputation-site limb;

melding the flopped moving image of the complementary portion of the subject's torso and its adjacent healthy limb, with the original moving image of the subject's healthy-side torso and limb; and, displaying the resultant composite moving image of the subject for subject's viewing, wherein the steps of acquiring the moving image, digital processing to obtain the composite moving image, and displaying of the composite moving image are performed without any substantial exertion by the subject.

According to yet another aspect of this invention, a system for alleviating phantom limb discomfort (PLP or PLS) in a subject's phantom limb or other body part comprising:

a smart phone for acquiring a moving image of a continuous portion of the subject that consists of the half-torso adjacent the limb of the amputation site and any remaining amputation-site limb, as well as acquiring a moving image of a continuous complementary portion of the torso and its adjacent healthy limb, in a particular mode of use;

a digital imaging program or application to obtain a composite moving image of the subject's body by deleting a moving image of the half-torso adjacent the limb of the amputation site and any remaining amputation-site limb, and placing a flopped moving image of a continuous complementary portion of the torso and its adjacent healthy limb, in the particular mode of use, in place of the deleted moving image of the half-torso adjacent the limb of the amputation site and any remaining amputation-site limb;

melding the flopped moving image of the complementary portion of the torso and its adjacent healthy limb with the original moving image of the healthy-side torso and limb; and, a smart phone for displaying the resultant composite moving image of the subject for subject's viewing, wherein the steps of acquiring the moving image, digital processing to obtain the composite moving image, and the displaying of the composite moving image are performed without any substantial exertion by the subject.

One aspect of this invention is the use of smart phones for acquiring images, for processing digital images to obtain composite images there from, and for displaying composite images to the subject for the purpose of alleviating phantom limb discomfort (PLP or PLS). This feature of the present invention is particularly useful in allowing the subject invention to be available at a negligible cost to a large number of people suffering from phantom limb discomfort (PLP or PLS). The use of smart phones also means that no specialists are needed. There is also no need for the subject to go to professional offices or a hospital to receive this therapy. By simply utilizing a smart phone with a mobile application or app, the subject can alleviate phantom limb discomfort in any setting.

FIG. 1 shows a subject 1 suffering from phantom limb discomfort (PLP or PLS) producing streaming digital imagery of himself as he faces the camera 4 of a smart phone 3. His right limb has experienced a hand-amputation 2. Throughout the phantom limb discomfort therapy, the program of the invention provides visual, voice, tonal, or other types of instructions, prompts, and cues on how to proceed in carrying out the therapy.

An adjustable diagrammatic outline-image 6 of a human male, on view-screen 5 of the smart phone guides the subject in situating himself in the proper relationship to the phone and camera so as to insure that his digital image 7, throughout the live-action streaming imagery produced by the smart phone, is correctly positioned within the above-mentioned diagrammatic image 6 of the human figure. The subject is informed by the program regarding the beginning of the digital-image recording, and is further instructed to remain relaxed while standing still. After about 10 seconds of footage of the subject standing still, the subject proceeds to perform a specific action with his fully intact left limb. The point in time when this specific action is to begin is signaled by another cue from the program. The subject is also instructed by the program to duplicate all the actions of his left arm and hand, to the extent he can, with his right arm and imagined right hand 2.

As a result of the specific type of phantom limb discomfort (PLP or PLS) endured by the subject in this example he is informed by the program to lift his left arm, which he has bent at the elbow. He is then instructed to do the same with his right arm. He is also instructed to perform, with his left hand, all those motions he most wants to experience in his phantom hand. He is now instructed to begin flexing the fingers of the left hand. Further, he is given instructions from the program, urging him to imagine performing with his phantom right hand, all the actions presently being undertaken by his left hand. This activity is continued for about 30 seconds, at which point a further cue signals the end of the streaming digital image-acquiring portion.

In a preferred embodiment, the following steps are performed without any substantial exertion by the subject. These steps are part of the program or application on the smart phone used for providing this therapy. The subject does not perform any continuous or concerted physical or mental exertion during these steps.

Figure 3:
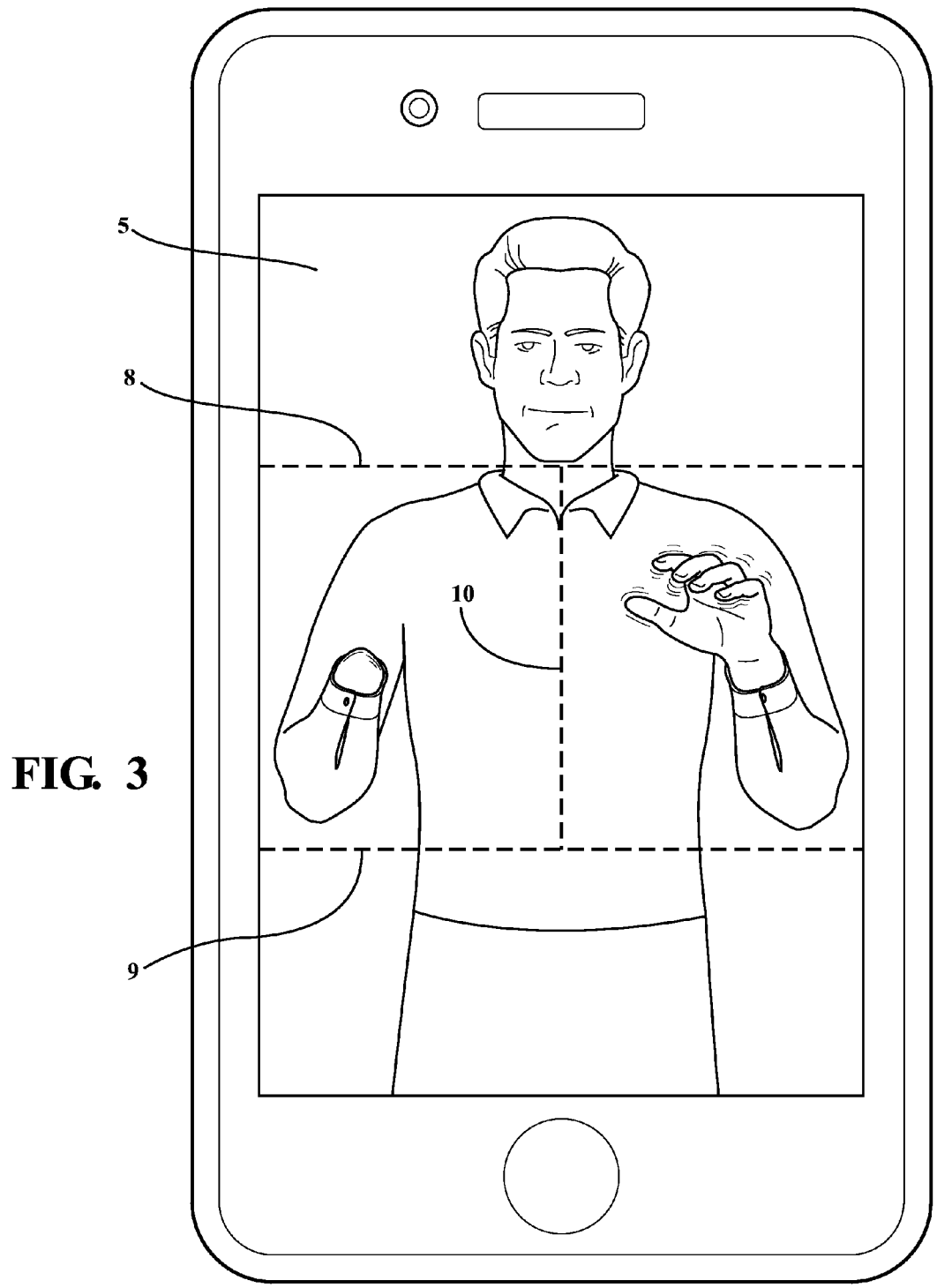
FIG. 3 is a view screen 5 of the smart phone showing the subject with both arms bent at the elbows, with the left hand raised to chest height. The subject's right arm is at the same height as the left arm; thus if subject had two hands, both would be in front of the subject's body. The subject is also shown flexing the fingers of his left hand. The figure also shows three adjustable bisection lines 8, 9, and 10 in place.
Figure 4:
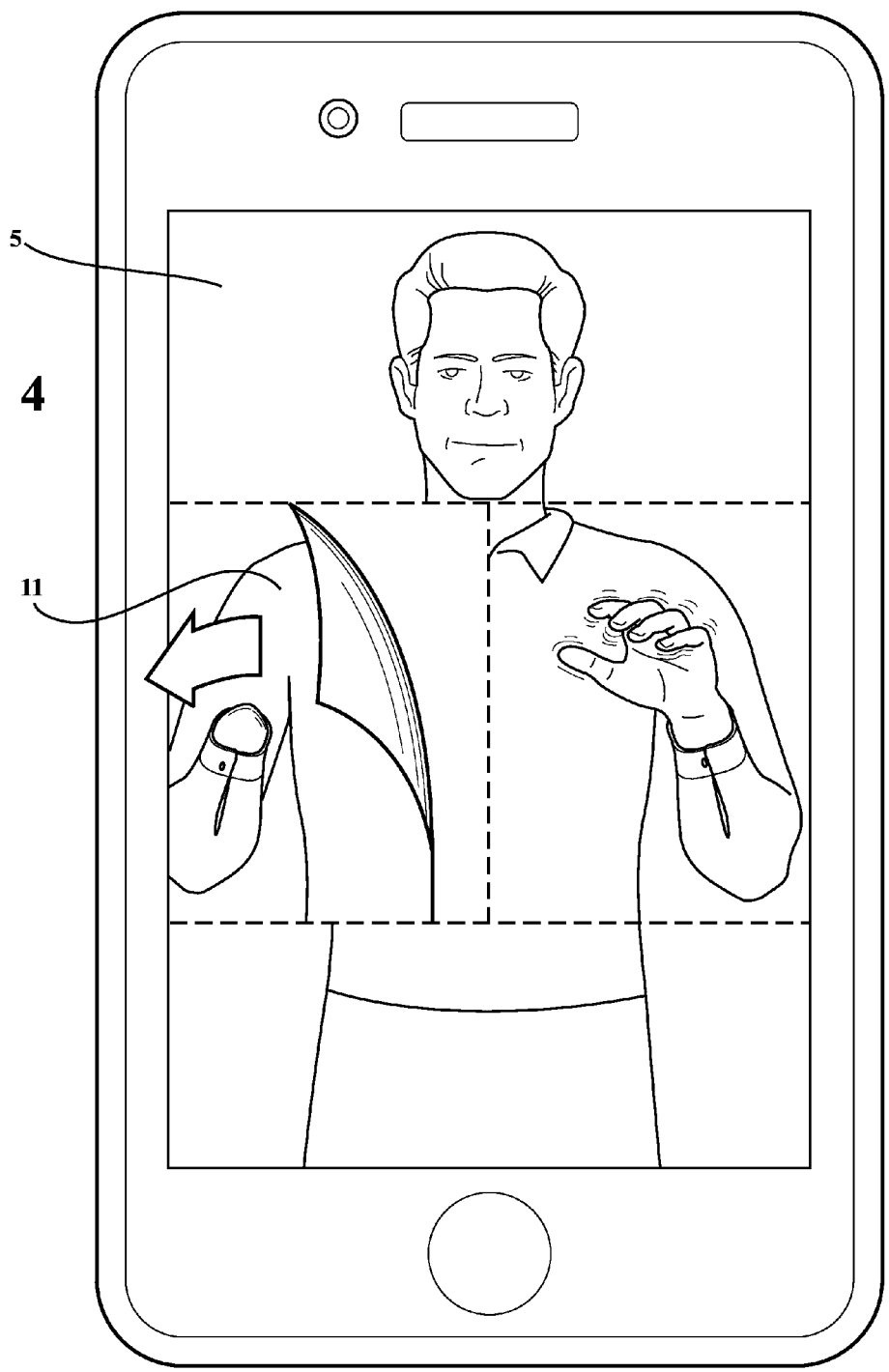
FIG. 4 is a view screen 5 of the smart phone showing the deleting of the right-hand side half-torso and limb 11 of the subject's digital image according to the bisection lines 8, 9, and 10.
Figure 4A:
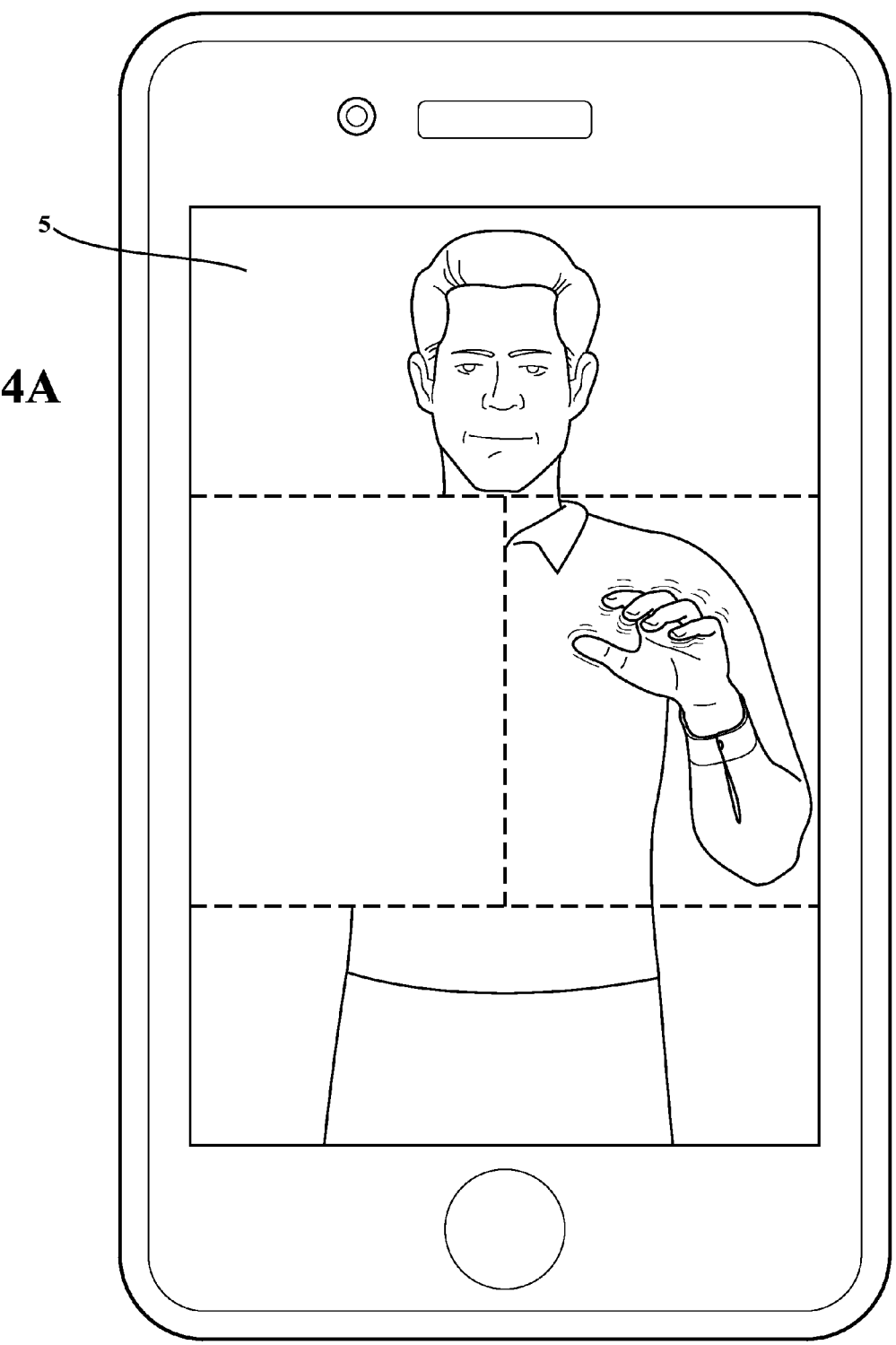
FIG. 4A shows view screen 5 of the smart phone. In the image shown here the right-hand side half-torso and limb 11 of the subject's digital image has been deleted according to the bisection lines 8, 9, and 10.

At first, the video of the subject's right-hand side half-torso and limb 11 is deleted by utilizing the necessary adjustable bisection lines. That is, using a vertical centerline 10 drawn on the subject's image as shown in FIG. 3, which line runs between two horizontal lines, a line 8 drawn across the individual at a level just above the shoulders, and the other line 9 drawn across the individual at a level below that of the two gesturing arms, the portion of the streaming video representing the subject's right-hand side half-torso and limb is selected and deleted. The selection and removal occurs as shown in FIG. 4 and FIG. 4A.

The position and selection of bisection lines is dependent on the subject's particular type of phantom limb therapy. In other words these lines and their position may be different for each type of phantom limb discomfort encountered. Specific instructions relative to a subject's type of phantom limb discomfort (PLP or PLS) are part of the smart phone's phantom limb discomfort-related program.

Figure 5:
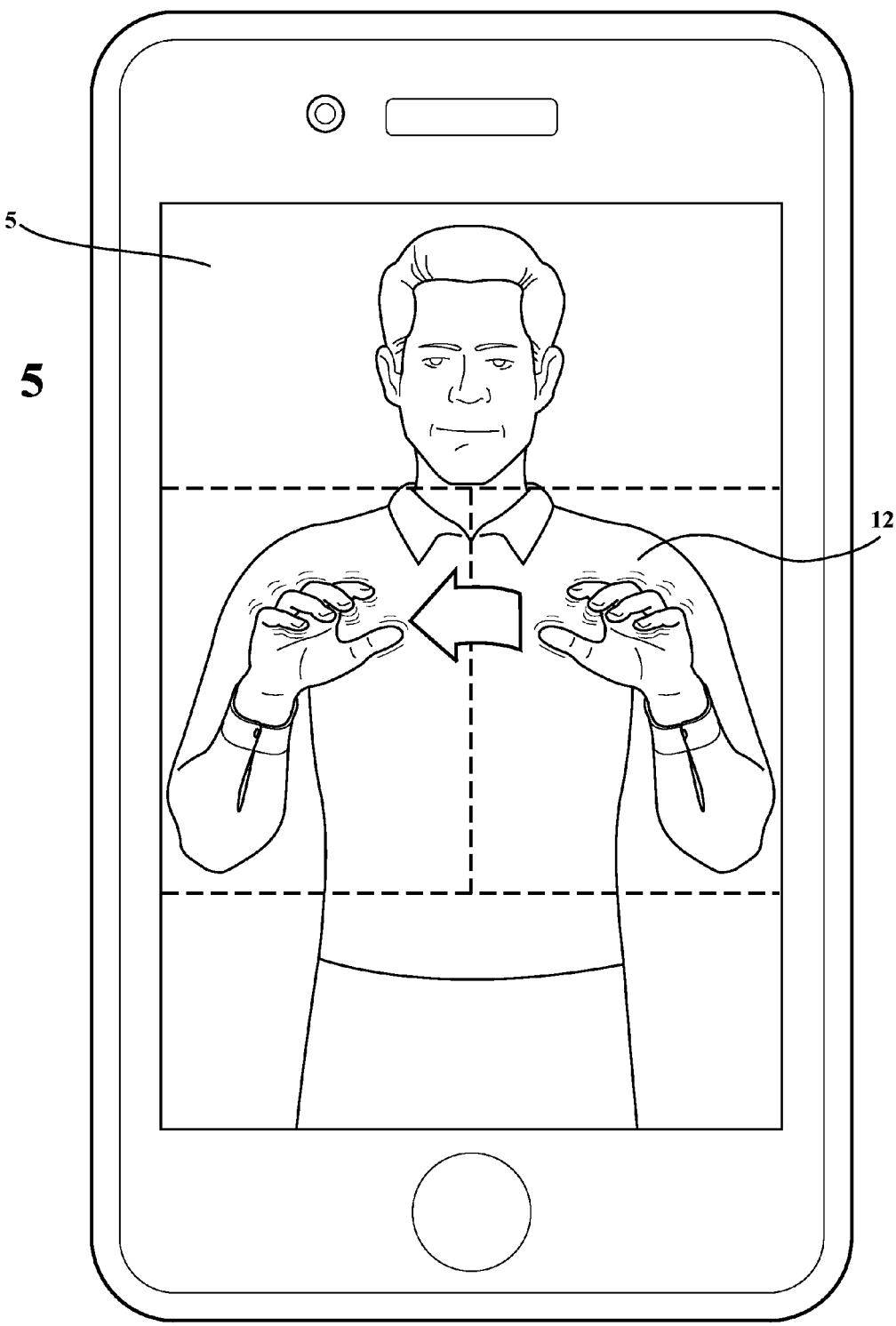
FIG. 5 shows the view-screen 5 of the smart phone. In the composite image shown here, the left-hand side half-torso and limb 12 of the subject's digital image has been flopped and placed where the subject's, now deleted, right-hand side half-torso and limb had been. This has been done in accordance with the bisection lines 8, 9, and 10. The left-hand side half-torso and limb imagery 12 is also maintained in its original position. Flopping describes the reversing of an image along a vertical axis. A flopped image may be said to be a mirror image of its respective original.

Next, the subject's left-hand side half-torso and limb imagery 12 is rotated 180 degrees, resulting in a minor image, also known as a flopped image; this image is substituted for the subject's now deleted right-hand side half-torso and limb imagery. The left-hand side half-torso and limb imagery is also maintained in its original position as shown in FIG. 5.

Figure 6:
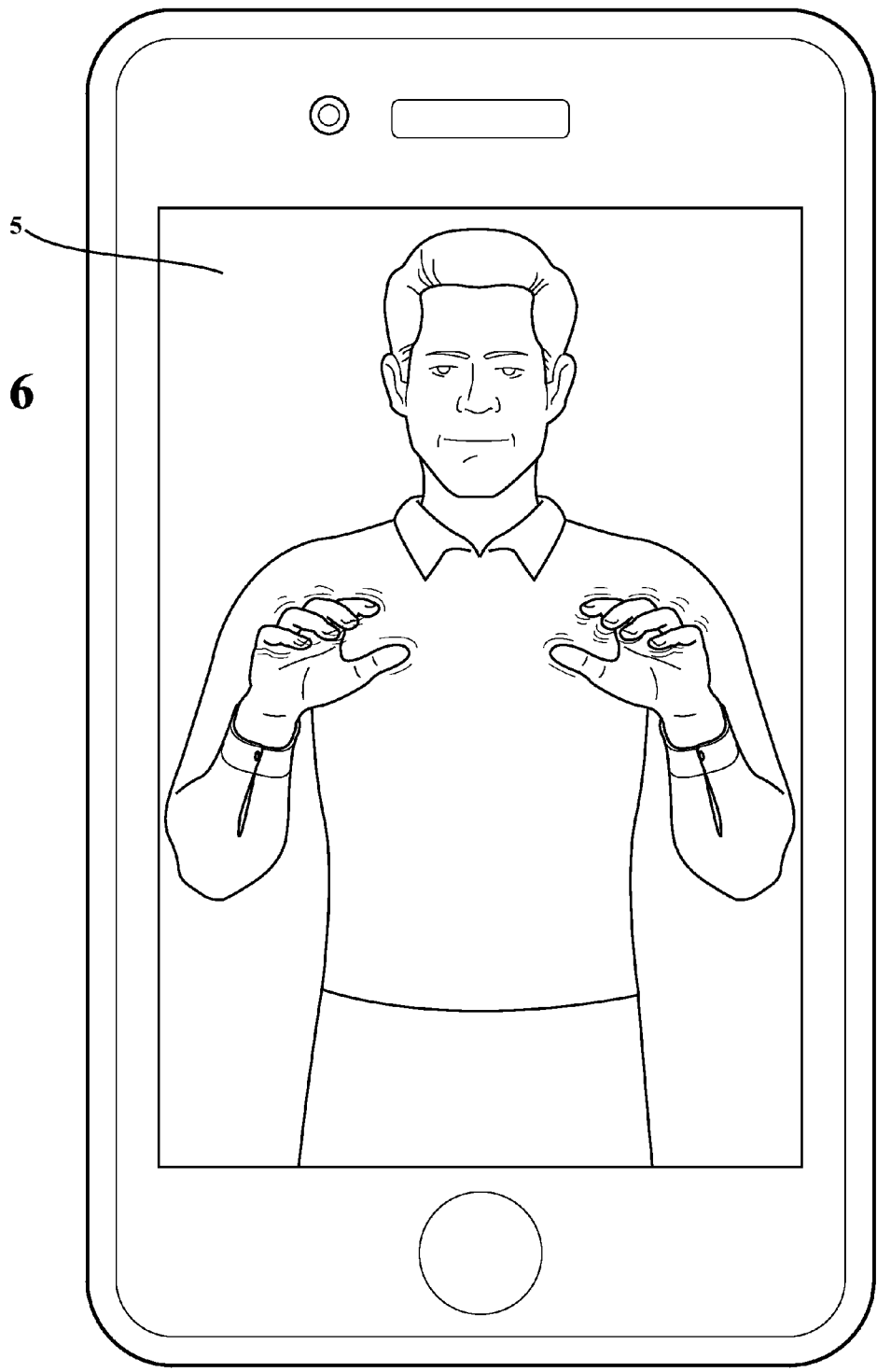
FIG. 6 shows view screen 5 of the smart phone with finished composite image of the subject. The phantom limb discomfort (PLP or PLS) sufferer's image appears on his smart phone's view screen, with both arms and hands fully intact, and without any artifacts used in the digital processing of the image. In this image, the subject is flexing the fingers of both hands.
Figure 7:
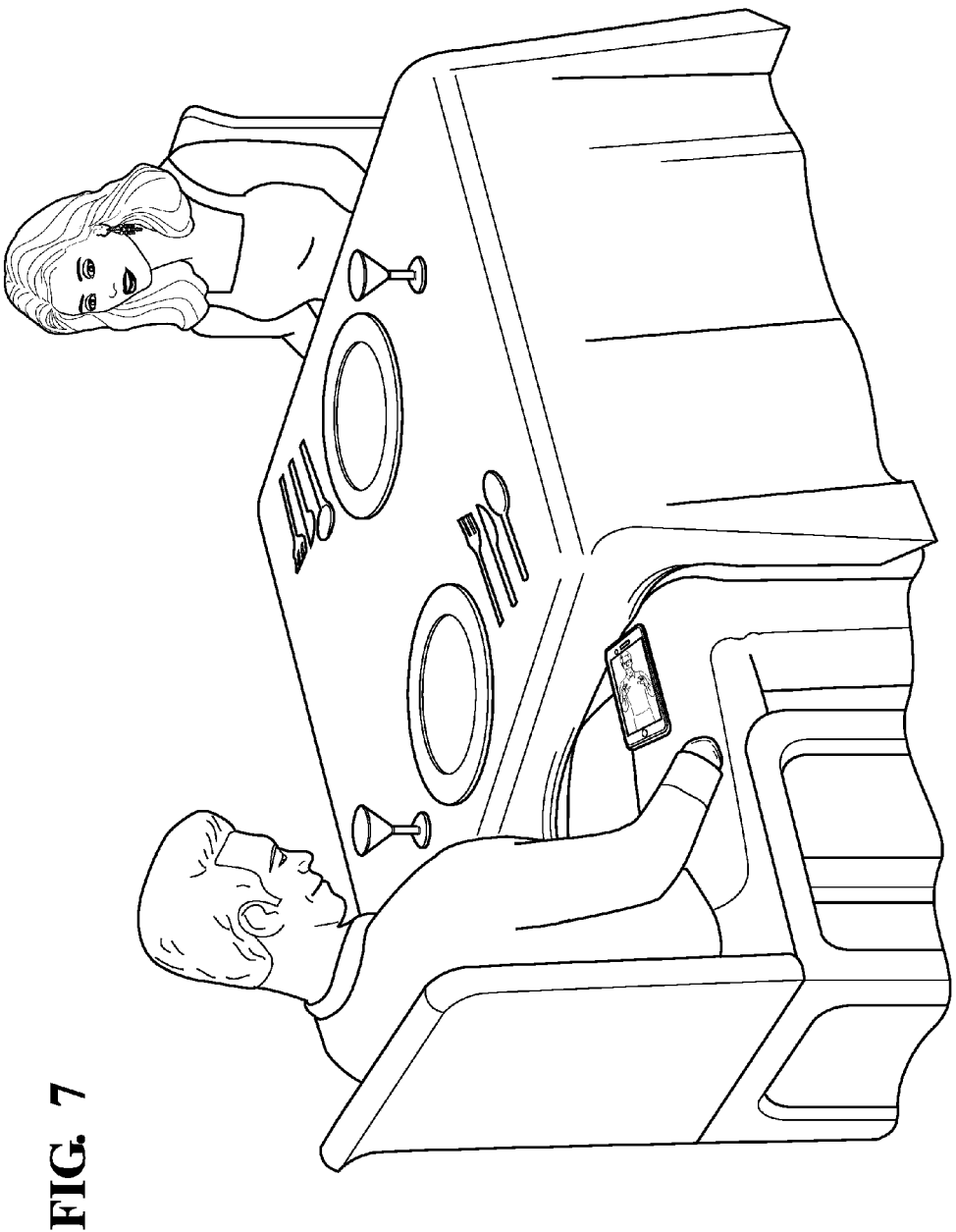
FIG. 7 shows the subject and a companion seated for a meal. The subject is viewing his composite image on his smart phone.
Figure 8:
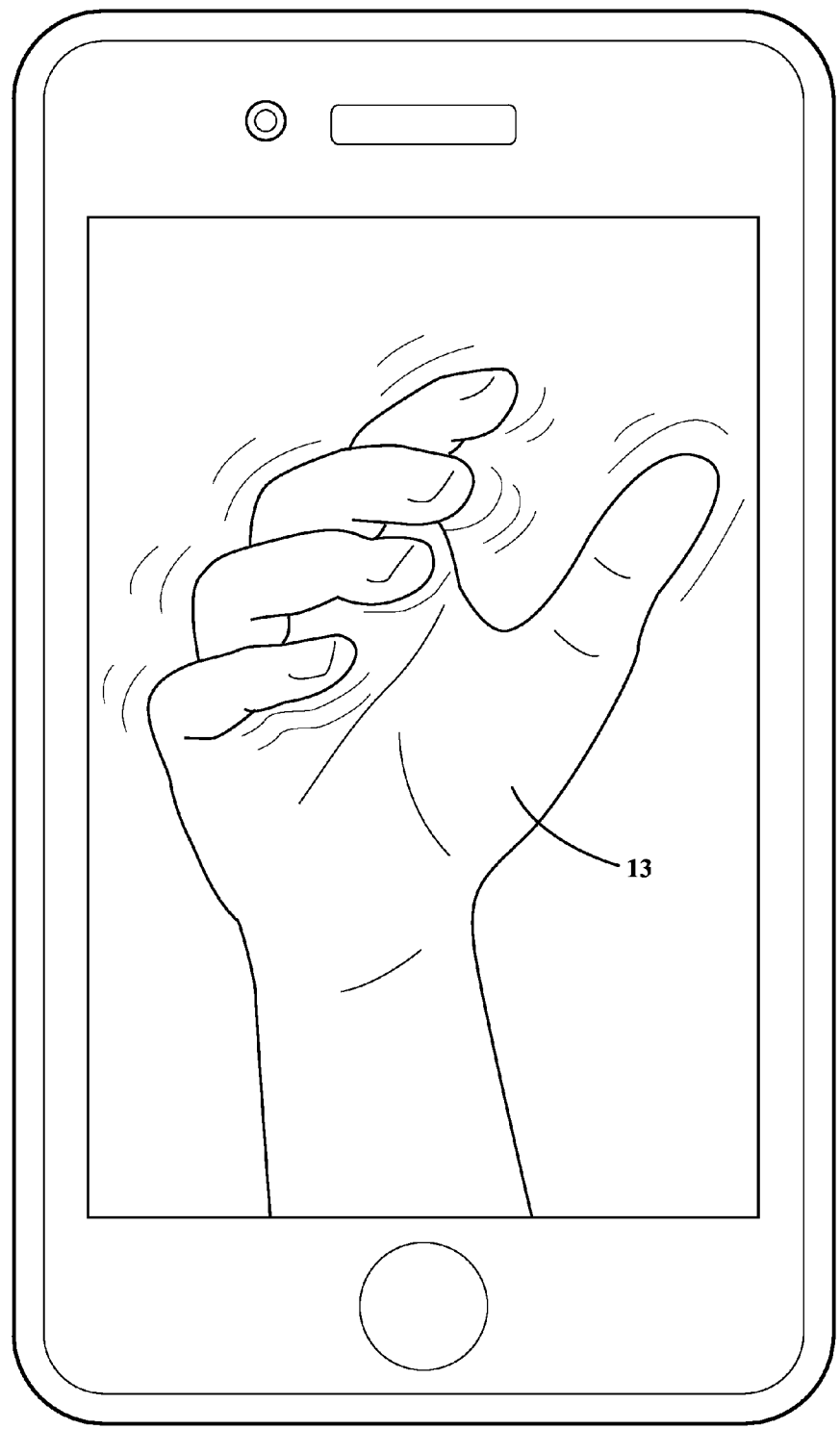
FIG. 8 shows a zoomed-in image of the subject's perceived right hand 13 on the view screen of the smart phone. This pictured hand is being therapeutically flexed in the digital-video production.

The program now melds, that is retouches all the necessary edges in the streaming imagery, which edges have resulted from the removal of a half-torso and limb and the flopping of a half-torso and limb. The completion of this melding, or stitching or patching, as this procedure is sometimes known, results in a very believable and therapeutic video of the subject. This imagery includes that of the subject's face, a very regular appearing torso, and two very believable arms and hands, as shown in FIG. 6.

The resulting 40-seconds of streaming digital imagery, with no diagrammatic outline and no bisection lines, is further edited by means of the program. As an example, five-seconds of the initial imagery, wherein the subject is standing still, is utilized at the beginning of the video. Further as example, this imagery is then allowed to fade to black. The next imagery is then allowed to fade-in. It is that of the subject with both arms raised, now beginning to vigorously flex the fingers of both hands. Still further as example, it is decided that 20-seconds of this therapeutic imagery is sufficient for alleviation of the subject's phantom limb discomfort (PLP or PLS). Therefore, at the end of the 20-seconds, the therapeutic imagery is allowed to fade to black.

In this example, then the final imagery consists of a stationary and relaxed subject at the beginning, followed by a presentation of the video's main portion showing the subject's image with both arms intact and raised, and next with both hands engaged in active flexing of the fingers. All the foregoing is presented on the view-screen of the smart phone. As the subject views this activity, he is visually concentrating on the displayed motions of the limb representing that side on which his phantom complaint occurs. Alleviation of his phantom limb discomfort (PLP or PLS) results from this viewing. As the realism of mirror therapy is highly effective as a means of achieving pain alleviation, so too is the realism of the present invention.

And with the present invention, aside from touch-responding to prompts on his view-screen, flexing the fingers on one of his hands constitutes the sum of the exertion needed to produce the subject's therapeutic treatment. As with minor therapy, the subject's phantom limb discomfort (PLP or PLS) is alleviated simply by his seeing the therapeutic imagery.

The alleviation of phantom limb discomfort (PLP or PLS) occurs using steps referred to as acquire, flop, meld, and view. The present invention's use of streaming video of the entire healthy-side digital representation of the subject's torso and limb, after flopping and melding, allows the subject to simply and readily achieve effective pain relief. The viewing of the flopped, minor-imagery leads to alleviation of phantom limb discomfort (PLP or PLS) somewhat like the therapeutic imagery of conventional mirror therapy.

The present invention, though, allows the subject to see his face depicted in the therapeutic imagery. Self-face recognition, as it is termed, is known to enhance efficacy in therapeutic imagery. In this respect, the present invention is more effective than minor therapy. In this same respect, it is also more effective than many forms of virtual reality therapy.

Further, all the desired therapy needed in addressing the subject's phantom limb discomfort (PLP or PLS), through the means of his merely attentive viewing of the very affordable and easily composed imagery, is made available to him in an extremely convenient manner on his nearby smart phone. No mirror is necessary and the therapy can be undertaken anywhere; the invention does not require the subject to leave the social setting in which he may be engaged at such time as phantom limb discomfort (PLP or PLS) presents.

The use of a smart phone with digital imaging programs or applications for alleviation of phantom limb discomfort (PLP or PLS), as described here, also allows the subject to customize the applications to allow for specific preferences. For example, if desired, the program or application subdues the right side of the image, from the height of the subject's shoulder down to the bottom of the image, utilizing the bisection centerline 10 in FIG. 3. Thus subdued, or ghosted, the image is now found to enhance the subject's desired concentration on the image's, thereafter, more prominent left side.

In another exemplary use of the invention, the program allows the right side of the image to be presented as a completely stilled, unmoving image appearing to show the subject, relaxed and motionless, left arm at his side. This could be the result of a single-image capture from the initial 10-second portion of the imagery, wherein the subject is shown standing still, being appropriately selected and melded for use on the right side of the imagery during the entire finished therapeutic video. This described approach is desirable for purposes of creating enhanced concentration by the subject on the left side of the image.

In yet another exemplary use of this invention, the program or application allows both segments of the video described above to be on-screen for longer times. The first segment, that of the individual standing still, is looped so as to be repeated as many times as desired. This is also done for the second segment, that segment comprising the images of the subject as he carries out the more active aspects of the instructions.

In the present invention, the therapeutic visual imagery is created by flopping the entire streaming visual imagery of the subject's healthy-side half-torso, including its respective shoulder, and arm. This visual imagery, when subsequently melded, presents a seamless, full-motion re-creation of the subject's complete normal-side half-torso and limb standing-in for the subject's phantom limb discomfort (PLP or PLS)-affected side.

In the present invention's final imagery, then, both half-torsos and their respective shoulders, are correctly and naturally portrayed relative to the imaged actions being taken up by their fully integrated and contiguous arms. Again, with the present invention, the program flops the entire streaming video segment of the subject's integrated and contiguous healthy-side half-torso, shoulder, and arm as they perform, in a believable and realistic manner, the desired therapeutic actions to be viewed. Every pixel within the flopped segment of the healthy-side half-torso, shoulder, and arm remains in the identical relative position to every other pixel in this healthy segment, as when said pixels were originally visually acquired.

In this manner, a choppy quality is avoided in the system and method of the present invention. The invention achieves a near-perfect, seamless presentation of its therapeutic imagery by flopping the subject's entire half-torso, including its respective shoulder, and arm. The entire pictured action is smooth and continuous. This believable delivery leads to enhanced self-recognition, relative to other proposed treatments that exhibit choppiness. Further, the present invention is achieved through the use of fast and affordable programs readily available on smart phones.

The melding that follows the flopping, described in the present embodiment, is done quickly and results in a visually convincing depiction. The process is aided by the use of the three bisection lines along which this melding occurs. All such needed bisection lines, called for by the varying types of phantom limb discomfort (PLP or PLS) that may present, are made available as an aspect of the program of the present invention. In the present embodiment, these bisection lines transect the human form through the neck, through a vertical mid-line of the torso, and through the abdomen, allowing for easy melding of the imagery. Additionally, this melding is made as efficient as possible by the nature of the subject's clothing and the nature of the background and lighting sought during the image-gathering aspect of the undertaking. All of these consideration as to clothing, background, and lighting are discussed fully in the program's instructions. Also, as stated before, the selection and position of these bisection lines is dependent on the type of phantom limb discomfort (PLP or PLS) being treated.

A subject may find the visual material, prepared for his use through the system and method of the present invention, to be of greater efficacy if the visual depiction of his right hand, that is, his amputated hand, now shown restored, is displayed on the right side of the view-screen, rather than on the left side. If such a change is desired, he may simply flop the entire prepared footage through a prompt within the program.

In a like manner, by flopping the prepared footage, the ghosted imagery on the view-screen's right side, and the stilled action on the view-screen's right side, as described earlier in this description, may both be, by prompts, seen taking place on the view-screen's left side.

The system and method of the present invention allows for the invention's use in dealing with phantom limb discomfort (PLP or PLS) in all of the manners in which they are known to present. These include phantom limb discomfort (PLP or PLS) experienced in full-arm amputation, and in partial-arm amputation including hand and finger amputation. Also included in the invention's use is phantom limb discomfort (PLP or PLS) experienced in full-leg amputation, and in partial-leg amputation, including foot amputation and toe amputation.

The present invention can also be used in cases of double-limb—that is both arms and or both legs (or both, or all, of any other body parts) either partial or entire—related phantom limb discomfort (PLP or PLS). This is achieved within the system and method of the present invention through the use of surrogate imagery, which surrogate imagery is to be either animated imagery, if necessary, or imagery obtained by visually recording the correct limb or limbs of an appropriate limb-double. As with earlier discussed imagery, this imagery will be processed and displayed in order to produce the desired therapeutic outcomes.

In one embodiment, any necessary animated imagery is obtained from a library of images provided with the smart phone's phantom limb discomfort program or application. This imagery is brought into the program and then manipulated in the same manner as that of the illustrative embodiment.

As noted earlier, phantom limb discomfort, either PLP or PLS, may be experienced as one or more of many various types of complaint, and within each of these types, the discomfort may range from mild to acute. Among the types of discomfort that are commonly perceived is a feeling like a mild electrical shock, or a feeling as if from a limb or body part that is being twisted, or crushed, or experiencing inappropriate distortion of limb-position. Clenching, cramping, itching, tingling, dampness, numbness, cold, heat, swelling, shrinking, and inappropriate motions such as swinging, are also often noted. Extreme discomforts, identified as that of burning, or extreme electrical shock, or searing pain, shooting pain, or pins and needles-like pain, as well as other types of pain, are also frequently reported.

The present invention can be used with all of the types of phantom limb discomfort (PLP or PLS) set out in the foregoing paragraph, as well as other types of phantom discomfort that may arise. This is done by means of input provided by the subject to the smart phone-based program or application. That is, through information inputs supplied by the subject, as well as through subsequent answers given to enquiries posed by the program, and next through prompts suggested by the program, an individualized therapeutic regimen is created for each subject. Such therapies work in the exact manner disclosed to this point: imagery is acquired, flopped where necessary, melded, and viewed by the subject. Used as well, when necessary, will be surrogate imagery, either animated imagery, or imagery created by visually recording the necessary therapeutically-indicated actions of a limb or limbs of an appropriate limb-double, which imagery will then be acquired, flopped where necessary, melded, and viewed.

Other aspects of phantom limb discomfort (PLP or PLS), treatable by the present system and method, are that of phantom breast pain and phantom breast sensation. This remediation is achieved in the identical manner as that utilized and disclosed in the above discussions of phantom limb discomfort (PLP or PLS). A woman, or in some cases a man, experiencing phantom breast discomfort due to the amputation of a breast, observes a digital presentation wherein her remaining breast has been visually flopped in the therapeutic video imagery. This makes possible the subject's seeing of herself with two breasts. She experiences remediation at the moment when, as just mentioned, she sees herself restored as she was prior to her amputation.

In one preferred embodiment, a particular type of phantom breast pain or phantom breast sensation may call for specific actions with which to address the remaining breast of a female subject. She is prompted to perform the appropriate remediating actions by the program, which is a part of the system and method of the present invention, as she is being visually, digitally recorded. Among these actions can be those of simply touching, rubbing, lifting, squeezing, or other specific actions applied to her breast as further possibilities that addressed during the woman's utilization of the program's prompts, which prompts are part of the program of the present invention. Subsequent manipulation of the recorded imagery, and next, its viewing, leads to the desired therapeutic outcome.

Even double-breast amputation-related phantom breast pain or phantom breast sensation is addressed by the system and method of the present invention through the use of surrogate imagery: either animated imagery, or imagery obtained by visually recording the appropriate breasts of a suitable breast-double. To achieve remediation of phantom breast pain, or phantom breast sensation, the subject observes the appropriately processed surrogate-enhanced imagery, as would any other sufferer of any other type of phantom limb discomfort (PLP or PLS).

Still another instance in which the system and method of the present invention can bring about the remediation of a phantom pain is that of phantom eye pain, also known as phantom eye syndrome. The present invention proposes to remediate such pain in that manner earlier discussed: one merely acquires, flops, melds, and views to achieve remediation of such pain or sensation.

Other types of discomfort where the present invention can play a therapeutic role are phantom organ pain or phantom organ sensation, as in the case of discomfort experienced subsequent to the loss of an external organ or organs, such as phantom tooth, phantom tongue, phantom nose, phantom ear, and phantom penis pain and sensation. Each of these pains or sensations is successfully treated in the manner described heretofore: one merely acquires, flops as necessary, melds, and views.

Regarding issues of phantom limb pain and phantom limb sensation pertaining to an organ of which humans have but one, the post-amputation therapy for phantom limb discomfort (PLP or PLS) of the present invention relies on surrogate imagery. This imagery is either animation, or imagery of an organ-double.

Another sort of phantom limb discomfort to be treated by the present invention is that pain or sensation resulting from a type of trauma termed learned paralysis. Additionally, Residual Limb Pain (RLP) will also be treated by the system and method of the present invention. RLP is a form of PLP.

Efficacy is also obtained, in phantom limb discomfort (PLP or PLS)-related complaints, by use of the present invention considered as an aspect of a Graded Motor Imagery program. The present invention augments or replaces the minor therapy segment of a Graded Motor Imagery program.

Additionally, the present invention can bring alleviation of discomfort in the following diseases and disorders: Chronic Pain, Chronic Impairment, Complex Regional Pain Syndrome, and Reflex Sympathetic Dystrophy. The present invention can also bring improved outcomes in some forms of paralysis resulting from stroke, including but not limited to, hemineglect. Improved outcomes, in a limb or limbs, can also be obtained in the treatment of some cases of diminished motor function arising from stroke, as well as in some cases of diminished control, in a limb or limbs, arising from stroke. Treatment in all of these conditions would be effected in the same manner as those described for treatment of phantom limb discomfort (PLP and PLS).

The present invention could also be produced with the involvement of 3-D technology, subsequently yielding a final video in 3-D.

It will be evident to those skilled in the art that the invention is not limited to the details of the foregoing illustrated embodiment and that the present invention may be embodied in other specific forms without departing from the spirit or essential attributes thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

It will also be understood that the system according to the invention may include a suitably programmed computer, which can be a smart phone. The system may also include a digital video recorder or camcorder, or a digital camera, or a Google Glass or Google Glass-type device. Likewise, the invention contemplates a computer program being readable by the computer for executing the method of the invention. The invention further contemplates a machine-readable memory tangibly embodying a program of instructions executable by the machine for executing the method of the invention.

What is claimed is:

1. A smart-phone based method for alleviating phantom limb discomfort in a subject with at least one phantom limb the method comprising:
   (a) acquiring a moving image of a continuous portion of the subject including at least a half-torso adjacent the at least one phantom limb, the at least one phantom limb, a half torso adjacent a complementary healthy limb corresponding to the at least one phantom limb, and the complementary healthy limb in a particular mode of use;
   (b) using a digital imaging program for obtaining a composite moving image of the subject by deleting a moving image of the half-torso adjacent the at least one phantom limb and the at least one phantom limb, and placing a flopped moving image of the half torso adjacent the complementary healthy limb corresponding to the at least one phantom limb and the complementary healthy limb in the particular mode of use in place of the deleted moving image, melding the flopped moving image where it abuts the continuous portion of the moving image of the half torso adjacent the complementary healthy limb wherein the complementary healthy limb has a portion that is unmodified; and
   (c) displaying the composite moving image of the subject for the subject's viewing, wherein the composite moving image is a therapeutic video, free of diagrammatic depictions, bisection lines, prompts and other program notes;
wherein steps (a), (b), and (c) are performed by a smart phone.

2. The method of claim 1 wherein the steps of acquiring the moving image, using the digital imaging program, and displaying of the composite moving image does not require continuous or concerted physical or mental exertion by the subject.

3. The method of claim 1 wherein the composite moving image includes facial imagery of the subject.

4. The method of claim 1 wherein the at least one phantom limb is selected from parts of human body consisting of a finger, hand, arm, toe, foot, leg, breast, eye, ear, nose, penis, tongue and tooth.

5. The method of claim 1 wherein the subject has at least two phantom limbs.

6. The method of claim 5 wherein the at least two phantom limbs are selected from parts of human body consisting of a finger, hand, arm, toe, foot, leg, breast, eye, ear and tooth.

7. The method of claim 1 wherein the complementary healthy limb is a surrogate limb.

8. The method of claim 1 wherein the phantom limb discomfort is due to disorders selected from the group consisting of Residual Limb Pain, Chronic Pain, Chronic Impairment, Complex Regional Pain Syndrome, stroke, learned paralysis, and Reflex Sympathetic Dystrophy.

\* \* \* \* \*

UNITED STATES PATENT AND TRADEMARK OFFICE
CERTIFICATE OF CORRECTION

| | | |
|---|---|---|
| PATENT NO. | : 8,911,343 B2 | Page 1 of 1 |
| APPLICATION NO. | : 13/656669 | |
| DATED | : December 16, 2014 | |
| INVENTOR(S) | : Wiest | |

It is certified that error appears in the above-identified patent and that said Letters Patent is hereby corrected as shown below:

In the Specification

Column 2, line 3 and column 4, line 29 and column 7, line 46 and column 8, line 23, 32 and 39 and column 11, line 64, for the word 'minor' each occurrence should read -- mirror --.

Signed and Sealed this
Thirtieth Day of June, 2015

Michelle K. Lee
*Director of the United States Patent and Trademark Office*